United States Patent [19]

Gallagher et al.

[11] Patent Number: 5,171,308

[45] Date of Patent: Dec. 15, 1992

[54] POLYESTERS AND THEIR USE IN COMPOSTABLE PRODUCTS SUCH AS DISPOSABLE DIAPERS

[75] Inventors: Francis G. Gallagher; Cathy J. Hamilton, both of Wilmington, Del.; Steven M. Hansen, Kinston, N.C.; Hyunkook Shin; Raymond F. Tietz, both of Wilmington, Del.

[73] Assignee: E. I. Du Pont de Nemours and Company, Wilmington, Del.

[21] Appl. No.: 834,794

[22] Filed: Feb. 13, 1992

Related U.S. Application Data

[63] Continuation-in-part of Ser. No. 769,414, Oct. 1, 1991, which is a continuation-in-part of Ser. No. 645,849, Feb. 15, 1991, Pat. No. 5,097,004, and a continuation-in-part of Ser. No. 645,995, Jan. 25, 1991, Pat. No. 5,097,005, and a continuation-in-part of Ser. No. 522,134, May 11, 1990, Pat. No. 5,053,482.

[51] Int. Cl.$^5$ .............. A61F 13/46; C08G 63/20; C08G 63/60; C08G 63/672

[52] U.S. Cl. .................. 604/372; 47/74; 220/DIG. 30; 428/35.5; 428/36.1; 428/36.4; 428/36.92; 428/287; 428/296; 428/480; 428/481; 521/182; 521/905; 528/300; 528/301; 528/302; 604/369; 604/372; 604/378; 604/383

[58] Field of Search .......... 528/300, 301, 302; 604/372, 378, 369, 383; 428/480, 481, 287, 296; 521/182, 905

[56] References Cited

U.S. PATENT DOCUMENTS

| | | | |
|---|---|---|---|
| 3,018,272 | 1/1962 | Griffing et al. | 528/293 |
| 3,385,831 | 1/1968 | Watson | 260/75 |
| 3,853,820 | 12/1974 | Vachon | 528/295 |
| 4,418,116 | 11/1983 | Scott | 428/288 |
| 4,483,976 | 11/1984 | Yamamoto et al. | 528/275 |
| 4,526,738 | 7/1985 | Miyoshi et al. | 428/369 |
| 4,883,706 | 11/1989 | Grosjean | 428/215 |
| 5,097,004 | 3/1992 | Gallagher et al. | 528/272 |
| 5,097,005 | 3/1992 | Tietz | 528/272 |

OTHER PUBLICATIONS

Ingamells, *J. Appl. Pol. Sci.*, vol. 26, 4087-4101 (1981).
Grassie, Developments in Polymer Degradation-5, 112-119 (1984), Applied Science Publishers.

*Primary Examiner*—James C. Cannon

[57] ABSTRACT

The invention provides novel polyesters, fibers and films, nonwovens from the fibers and disposable products of the polyesters such as diapers. The products are degradable under the conditions typically existing in waste composting processes, have low ingredient costs and yet provide strength and toughness properties adequate for end uses such as in disposable diapers. The polyesters are based upon polyethylene terephthalate copolymerized with a non-aromatic diacid, such as adipic and glutaric acids, and containing alkali metal or alkaline earth metal sulfo groups, such as a metal 5-sulfoisophthalic acid derivative.

9 Claims, No Drawings

POLYESTERS AND THEIR USE IN COMPOSTABLE PRODUCTS SUCH AS DISPOSABLE DIAPERS

CROSS-REFERENCE TO RELATED APPLICATIONS

This application is a continuation-in-part of our co-pending application Ser. No. 07/769,414, filed Oct. 1, 1991, which is itself a continuation-in-part of the co-pending application filed by Gallagher, Hamilton and Tietz as Ser. No. 07/645,849, now U.S. Pat. No. 5,097,004, and of the copending application filed by Tietz as Ser. No. 07/645,995, now U.S. Pat. No. 5,097,005, both filed Jan. 25, 1991, and a continuation-in-part of copending parent application Ser. No. 07/522,134, filed by Tietz, May 11, 1990, U.S. Pat. No. 5,053,482.

FIELD OF THE INVENTION

This invention relates novel polyesters and products therefrom. The products include fibers, films, foams, coated papers, extruded nets, molded objects and non-wovens and disposable products such as diapers from such products. The products are degradable to innocuous material under conditions used in municipal solid waste composting systems.

BACKGROUND OF THE INVENTION

The inadequate treatment of municipal solid waste which is being put in landfills and the increasing addition of nondegradable materials, including plastics, to the municipal solid waste streams are combining to reduce drastically the number of landfills available and to increase the costs of municipal solid waste disposal. While the recycling of reusable components of the waste stream is desirable in many instances, there are some products which do not readily fit into this framework, e.g. disposable personal absorbents such as diapers and sanitary napkins, garbage bags, and numerous other products. The composting of non-recyclable solid waste is a recognized and growing method of reducing solid waste volume for landfilling and/or making a useful product from the waste to improve the fertility of fields and gardens. One of the limitations to marketing such compost is the visible contamination by undegraded plastic such as film and fiber fragments.

As related in the aforesaid parent applications, which are hereby specifically incorporated herein by reference, there was a desired to achieve several objectives, as follows:

1—to provide components which are useful in disposable products and which are degraded into less contaminating forms under the conditions typically existing in waste composting processes. These conditions may involve temperatures no higher than 70 C., and averaging more nearly 55-60 C., humid conditions as high as 100% relative humidity, and exposure times which range from two weeks to more than three months.

2—to provide disposable components which will not only degrade aerobically/anaerobically in composting, but will continue to degrade in the soil or landfill. As long as water is present, they will continue to break down into low molecular weight fragments which can be ultimately biodegraded by microorganisms completely into biogas, biomass and liquid leachate, as for natural organics like wood.

3—to provide novel polyesters for making the aforementioned fibers, films, coatings and nonwoven sheets of the polyesters, and disposable diapers containing the nonwoven sheets.

4—to provide polyesters and derivative products which have low ingredient costs and yet provide strength and toughness properties adequate for end uses such as in disposable diapers.

Accordingly, as described therein, useful novel polyesters were provided and fibers, non-woven sheet, films and combinations thereof, and disposable diapers comprising such materials. Such polyesters are useful for some end uses, e.g., as described. It would, however, be desirable to provide additional degradable materials, having properties that may be better adapted for various end uses. In particular, it is desirable to provide additional polyesters that can be formed into films that have good toughness, with similar advantageous properties in many respects, and polyesters having good rates of hydrolysis.

Abbreviations and nomenclature herein, except as otherwise indicated, are as described in aforesaid U.S. Pat. No. 5,053,482, and Applications Ser. Nos. 07/645,849 and 07/645,995, mentioned above, and pending applications Ser. Nos. 07/769,417 and 07/771,019 filed Oct. 1, 1991, all of which are hereby incorporated herein by reference, as are applications Ser. Nos. 834,795, 834,796, 834,793, 834,791, 834,792 and 834,797, being filed at the present time.

DESCRIPTION OF RELATED ART

Various polyester compositions have been suggested in the past for biodegradable end uses. These include polyhydroxybutyrate, polylactide, polycaprolactone, polyglycolide, and their copolymers. They have not been widely adopted in high volume uses, however, because they are either too expensive or their properties are inadequate for the uses mentioned above.

It is known to use salts of 5-sulfoisophthalic acid and its esters as comonomers to improve acid dyeability of polyethylene terephthalate fibers, see for example U.S. Pat. No. 3,018,272 (Griffing et al.). Moreover, this type of fiber is known to have an increased rate of hydrolytic degradation, see for example J. Appl. Poly. Sci., vol. 26, 4087–4094 (W. Ingamells et al.) and Developments in Polymer Degradation 5, edited by N. Grassie, Applied Science Publishers, 1984, pp. 112–119. The use of 5-sulfoisophthalic salts together with other neutral comonomers has been disclosed to increase dye rates, but the proportion of the neutral comonomer is usually minimized to affect physical properties as little as possible, see for example U.S. Pat. Nos. 4,704,329 (Hancock et al.) and 3,853,820 (Vachon).

It is also known to use as much as 20 to 45 mole % diethylene glycol as a comonomer with ethylene glycol and terephthalic to provide polyesters having suitable melting and bonding characteristics for a nonwoven binder fiber, see for example U.S. Pat. No. 4,418,116 (Scott). Further, it is known to prepare water dispersible papermaking binder fibers which are made containing 5 to 20 mole % of diethylene glycol and preferably more than 3 mole % 5-sulfoisophthalate, see for example U.S. Pat. No. 4,483,976 (Yamamoto et al.). In the latter patent each of the specific polymers disclosed contain 7 mole % or more of the 5-sulfoisophthalate salt.

SUMMARY OF THE INVENTION

The present invention is based on our finding that polyesters of the aforesaid copending applications may be advantageously modified by including in the molecule, usually instead of part of the para-phenylene (T) units, a proportion of a non-aromatic acid, such as adipic acid.

In one embodiment of the invention there is, accordingly, provided a novel fiber and film forming polyester consisting essentially of recurring structural units of the Formula (I)

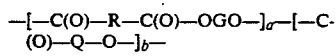

wherein about 5 to 40 mole % of R is selected from the group consisting of a chemical bond and one or more divalent, non-aromatic, $C_1$-$C_{10}$ hydrocarbylene radicals, and the remainder of R is at least about 85 mole % p-phenylene radical, wherein G is about 1 to 30 mole % of a polyethylene ether radical selected from the group consisting of —$(CH_2)_2$—O—$(CH_2)_2$— and —$(CH_2)_2$—O—$(CH_2)_2$—O—$(CH_2)_2$— the remainder of G is a hydrocarbylene radical selected from the group consisting of —$(CH_2)_2$—, —$(CH_2)_3$—, and —$(CH_2)_4$-radicals, wherein Q is derived from an hydroxy acid of formula HO[—C(O)—Q—O—]$_x$H, where x is an integer, such hydroxy acid having a melting point at least 5 C. below its decomposition temperature, and is selected from the group consisting of a chemical bond and hydrocarbylene radicals, —$(CH_2)_n$—, where n is an integer from 1 to 5, —C(R')H—, and —C(R')HCH$_2$—, wherein R' is selected from the group of —$CH_3$ and —$CH_2CH_3$, with the aforesaid hydroxy acids and polyhydroxy acids and copolyesters therefrom being more fully described in application Ser. No. 07/645,995, wherein the mole fraction "a" may be 0.6 to 1 and, correspondingly, mole fraction "b" may be 0 to 0.4, and wherein about 0.1 to about 2.5 mole % of the polymer contains alkali metal or alkaline earth metal sulfo groups, preferably as a sodium 5-sulfoisophthaloyl radical, especially about 1.5 to about 2 mole % of such groups.

If desired, some of the G may be a radical of a polyalkylene glycol of (number average) molecular weight (MW) at least about 250, as disclosed in copending application Ser. No. 07/645,849, e.g. polyethylene glycol (PEG).

Other embodiments of the invention include fibers, foams, films and coatings of the above polyesters and nonwovens of the fibers. The invention also contemplates disposable products, such as diapers, which contain an absorbent body portion, with, on at least one surface, a water permeable nonwoven sheet composed of the polyester fibers, a water impermeable film of the polyester, or a combination thereof.

It is a finding of the invention that such polyesters, derived from non-aromatic dibasic acids, such as adipic acid (abbreviation 6) and glutaric acid (abbreviation 5), as well as from terephthalic acid (abbreviation T), a metal salt of a b 5-suloisophthalic acid (abbreviation 5SI), ethylene glycol (abbreviation 2G) or other lower alkylene glycol (such as 3G and 4G), and polyethylene ether glycols (abbreviations DEG or TEG), and, if desired, a $C_2$-$C_4$ polyalkylene ether glycol of the indicated higher molecular weight (such as PEG), undergo degradation when subjected to the conditions of moisture and temperature that typically characterize composting operations. It is also significant that the bulk of the monomers resulting from degradation, i.e. the acids and the glycols, are readily digested by organisms in solid waste or compost to create carbon dioxide, methane and water.

A preferred polyester of the invention is that indicated by the abbreviation 2G/DEG-T/5SI/5 and/or 6, containing up to 20 mole % of DEG, and containing 1.5 to 2 mole % of 5SI and 10 to 40 mole % of adipic and/or glutaric acid. As in the aforesaid applications, numbers are used to connote the mole percentages of the glycol and of the diacid monomeric units in the polyester, while any PEG content may be denoted in weight (W) % of the total polymer, if so indicated, or by numbers like the other mole percentages if not so indicated.

These polyesters provide useful materials having applications in end uses where containment of body fluids is necessary and disposability is desirable, e.g., in a degradable film or in a fabric or paper coated with a film which will conform easily to body contours yet act as an effective barrier to penetration of body fluids. It is especially preferred that such films or coated sheets should have a reduced tendency to rattle and rustle when flexed during body movements. Such a film or coated sheet must have adequate strength and toughness to allow its survival during use. In order that it not leave objectionable residues when disposed of, it should disintegrate quickly when placed in proper waste disposal facilities and, ultimately, degrade substantially completely to innocuous materials, such as carbon dioxide, methane and water.

Many copolyesters which are copolymerized with 5-sulfoisophthalic acid (5SI) will hydrolyze readily. Not all such copolymers are acceptable in the end uses contemplated. The polymers should exhibit the desired physical properties, and be processable under practical conditions, but the products of hydrolysis should desirably have the potential to be digested by the organisms likely to be found is waste disposal facilities and compost. This cannot be achieved by all monomers used in preparing other copolyesters. We have found, for example, that terephthalic acid is decomposed substantially completely in such a test over 28 days, and that ehtylene glycol and polyethylene glycol (with MW 250 and 3500) are also satisfactorily digested by organisms typical of those found in waste disposal systems; typically, as the molecular weight increases, degradation generally becomes slower. Our non-aromatic acids (such as adipic acid and glutaric acid) are known to be decomposed rapidly, and carbonic acid gives carbon dioxide and water directly. Sodium dimethyl 5-sulfoisophthalate, which has shown slower degradation in these tests, constitutes only a very small proportion of the copolymers. 4-sulfophthalic acid (4SP) has been used instead of 5SI in related compositions, and has shown complete decomposition in certain test, so many sometimes be preferred, if this is an important consideration. In this regard, it should be recognised that the rate and extent of decomposition is affected significantly by selection of particular organisms and other specifics during composting.

As indicated, if desired, according to the invention, hydroxy acid residues may be incorporated. This may be effected by transesterification carefully to provide copolyesters containing, by weight of the copolyester, at least about 60% of glycol/diacid polyester as discussed and illustrated in first part of Formula (I) with up to about 40% consisting essentially of structural units of the formula [—C(O)—Q—O—], and wherein Q is such that the hydroxy acid HO—C(O)—Q—OH, which may be a polyhydroxy acid, has a melting point at least 5 C. below its decomposition temperature, and Q is preferably —CH$_2$—, —CH$_2$—CH$_2$—, —CH$_2$—CH$_2$—CH$_2$—, —(CH$_2$)$_5$—, —C(CH$_3$)H—, or —C(R')H—CH$_2$—, where R' is selected from the group of —CH$_3$ and —CH$_2$—CH$_3$, similar to the copolyesters more fully described in aforesaid application Ser. No. 07/645,995.

DETAILED DESCRIPTION OF PREFERRED EMBODIMENTS

The polyesters of the invention consist essentially of recurring structural units of Formula I

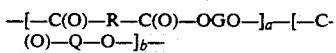

wherein about 5 to 40 mole % of R is selected from the group consisting of a chemical bond and one or more divalent, non-aromatic, C$_1$-C$_{10}$ hydrocarbon radicals, and the remainder of R is at least about 85 mole % p-phenylene radical, wherein G is about 1 to 30 mole % of a polyethylene ether radical selected from the group consisting of —(CH$_2$)$_2$—O—(CH$_2$)$_2$— and —(CH$_2$)$_2$—O—(CH$_2$)$_2$—O—(CH$_2$)$_2$— the remainder of G is a hydrocarbylene radical selected from the group consisting of —(CH$_2$)$_2$—, —(CH$_2$)$_3$—, and —(CH$_2$)$_4$— radicals, wherein Q is derived from an hydroxy acid of formula HO[—C(O)—Q—O—]$_x$H, where x is an integer, having a melting point at least 5 C. below its decomposition temperature, and Q is selected from the group consisting of a chemical bond and hydrocarbylene radicals, —(CH$_2$)$_n$—, where n is an integer from 1 to 5,—C(R')H—, and —C(R')HCH$_2$—, wherein R' is selected from the group of —CH$_3$ and —CH$_2$CH$_3$, with the aforesaid hydroxy acids and polyhydroxy acids and copolyesters therefrom being more fully described in application Ser. No. 07/645,995, wherein the mole fraction "a" may be 0.6 to 1 and, correspondingly, mole fraction "b" may be 0 to 0.4, and wherein about 0.1 to about 2.5 mole % of the polymer contains alkali metal or alkaline earth metal sulfo groups, preferably as a sodium 5-sulfoisophthaloyl radical, especially about 1.5 to about 2 mole % of such groups.

Thus, of the R radicals, about 5 to 40 mole % should be an alkylene or other residue from an organic C$_2$-C$_{12}$ non aromatic dibasic acid, with at least about 85 mole % of the remainder (about 60 to 95 mole %) being T (paraphenylene), with optional inclusion of up to about 15% mole % of I (meta-phenylene).

Of the G radicals, about 1 to 30 mole % are preferably DEG and/or TEG (i.e., polyethylene ether radicals —(CH$_2$)$_2$—O—(CH$_2$)$_2$— and —(CH$_2$)$_2$—O—(CH$_2$)$_2$—O—(CH$_2$)$_2$—, respectively). Optionally, if desired, some may be PEG (a radical of a polyalkylene glycol of MW at least about 250), with the remainder being 2G, 3G and/or 4G (i.e. C$_2$-C$_4$ lower alkylene groups).

Any Q radicals are from an hydroxy acid, as indicated above.

Importantly, the polymer contains sulfo groups, such as are described in U.S. Pat. No. 3,018,272 (Griffing and Remington), the disclosure of which is hereby incorporated by reference. The amount of sulfo groups in the polymer should be about 0.1 to 2.5 mole %. Thus, about 0.1 to 2.5 mole % of the R may be 5SI and/or 4SP radicals, as described herein, or may be another sulfo group suggested by Griffing et al. Or, if desired, about 0.1 to 2.5 mole % of the G may be the sulfo group. Thus the content of sulfo group-containing radical is calculated with respect to the recurring structural units of the formula [—C(O)—R—C(O)—OGO—]. Such radicals may, however, be contained in other units, i.e., other than in the R or G units, for instance in end groups, if desired. The radicals containing sulfo groups need not necessarily be aromatic, although 5SI and 4SP have given good results. Preferred amounts are about 1.5 to 2 mole %.

The polyesters of the invention are not soluble in water (in contrast to like polyesters derivable from the same constituents but with very much higher mole percentages of 5SI). They also have relatively low glass transition temperatures, Tg.

Thus, advantageously the Tg of the polyester fibers or films should be no higher than approximately the temperature at which degradation will take place. Since the temperatures in composing operations are often no higher than about 70 C., it is desired that the Tg of the polyester be no more than about 70 C., preferably about 65 C. or below. Commercial unmodified polyethylene terephthalate (abbreviation 2GT) polyester fibers have a Tg of about 80 C. Even a 2G-T polyester containing 2.5 mole % of 5SI has a Tg value of 76 C. The replacement of some terephthalic acid with an aliphatic acid, such as azelaic, succinic, adipic, sebacic or glutaric acid, is advantageous in lowering the Tg.

The organic non-aromatic dibasic acid is preferably adipic and/or glutaric acid, but may azelaic, succinic, sebacic or other acid, ranging from oxalic acid (C$_2$) to dodecanoic acid (C$_{12}$), as dibasic acids having larger numbers of carbon atoms are not yet commercially available. The aforesaid parent applications provide for incorporating small amounts of such aliphatic acids. The more of such acid that is added, the more significant is the effect of such incorporation. It is not, however, desirable to lower the melting point of the polymer to such an extent as to impair its usefulness, depending on the desired end-use, and it is generally desirable to incorporate no more than about 40 mole % of such acid. Preferred amounts are 10-30 mole %.

It will be understood that, with minor variations in composition, it is possible for the polyesters of the invention to have a further significant reduction in their Tg values. For example, the replacement of up to 5 mole % of the ethylene glycol with a polyethylene ether glycol, such as DEG or TEG (triethylene glycol), can also lower the Tg. Such amounts will not otherwise materially alter the degradation characteristics of the polyesters, hence their inclusion is contemplated by the term "consisting essentially" used to describe the polyesters and other products of the invention.

Minor amounts of polyfunctional branching agents, such as trimellitic acid residues, may be incorporated to modify melt rheology and film processing, if desired.

The glycol component may advantageously contain a polyethylene ether radical, such as DEG or TEG, to achieve an optimum level of degradability without a major sacrifice to fiber and film physical properties such as tensile strength. Above about 40 mole % DEG such properties are adversely affected, as indicated by Tietz.

The acid component preferably includes about 1.5 to 2 mole % 5SI. This component is not only relatively costly but also excessively large amounts can render the polyesters water soluble and thus affect the fiber and film physical properties such as shrinkage. As little as 0.1 mole % of 5SI contributes significantly to the degradability characteristics of the resultant fibers and films. Alternatively, as indicated, other sulfo group-containing units may be included, as taught in U.S. Pat. No. 3,018,272. In such monomeric units, the metal ion is preferably an alkali metal such as sodium, potassium or lithium. However, alkaline earth metals such as magnesium are also useful. A 5-sulfoisophthalate that have given very good results is the sodium salt.

A relative viscosity of at least 16, preferably at least about 18, is generally acceptable for melt spinning performance.

The polyesters of the invention may be prepared by conventional polycondensation techniques using, for example, as the glycol component, a combination of about 15 to 20% by weight of the polyalkylene glycol, with a complemental molecular amount of ethylene glycol, and, as the acid component, a combination of about 10 to 40 mole % of the non-aromatic acid, about 57 to 89.9 mole % of terephthalic acid and about 0.1 to 2.5 mole % of a metal salt of 5-sulfoisophthalic acid, which is preferred component containing the sulfo groups. Any carbonic acid residues are conveniently introduced by transesterification. Optionally up to about 5 mole % of the ethylene glycol can be replaced by another glycol. In lieu of the mentioned dicarboxylic acids, ester-forming derivatives such as the dimethyl esters of the acids may be used.

In the Examples herein, the various monomeric components are charged to a polymerization vessel along with an antimony or other catalyst and subjected to polycondensation conditions to produce a linear polyester in which the units are randomly distributed along the molecular chain. It will be understood that it is also possible, however, to first react two or more of the monomeric components to a prepolymer stage, followed by addition of the remaining components, which may be polymeric, such as polyethylene adipate, polylactide, polyglycolide or polycaprolactone, and completion of the polymerization.

The polyesters of the invention are very hydraulically sensitive, having a higher equilibrium moisture contents than 2G-T resin and a faster moisture regain rate. It is desirable that isolated flake be dried thoroughly, preferably to a moisture content below 400 ppm before reextrusion, and to maintain a nitrogen atmosphere around all possible air in leakage points, and to transfer polymer in warm condition (e.g., above about 50 C.) from the dryer to the extruder.

The polyesters as isolated from the reactor usually have multiple melting points by DSC analysis. These are seen at temperatures which overlap those which might be used in drying 2G-T flake, making it difficult to dry these polymers without fusing the flake into a solid mass when they are rapidly heated to get fast economical drying rates. Slower heating to allow crystallization, after which heating at higher temperatures for fast drying, is desirable.

A desirable procedure for preparing high molecular weight resins from rapidly polymerized lower molecular weight ones may be to use solid phase polymerization of low molecular weight flake. This procedure may desirably be carried out after or in combination with the crystallization procedure mentioned above so that temperatures high enough for rapid polymerization can be attained without fusing of the flaked resin. In addition, as known from U.S. Pat. No. 3,544,523, anticaking agents may be useful to prevent sticking, such as Cab-o-sil grade MS-75D, or other finely divided inert solids, like $TiO_2$, talc, carbon black and clay.

It is desired, for environmental or other reasons, to avoid use of a catalyst that comprises antimony or another heavy metal, then this may be achieved, for instance, by using a crystalline sodium aluminosilicate molecular sieve such as Linde Molecular Sieve 13X, type 9356, with a nominal pore size of 10 A, obtained from Union Carbide Corporation. Such procedure is more fully described "by Jackson in U.S. Pat. No. 5,041,525, issued Aug. 20, 1991," but other methods of avoiding antimony may be used, if desired.

In any event, the particular mole percentages of the aforementioned components are desirably selected to provide a polyester which in fiber or film form has a Tg of 70 C. or less, preferably of about 65 C. or less.

As will be understood, while the polyesters of the invention are well suited for use as fibers or filaments in nonwoven sheets, they can be used to particular advantage in the form of cast and blown films, foams, coatings, laminates, molded articles, or wherever polyesters with such properties are desired.

Fibers and filaments herein are interchangeable terms in the general sense, but where a more specific acknowledgement of length is appropriate, the term "fibers" is intended to refer to short filaments as in "staple fibers". Hereafter only one of the terms may be used.

The polyesters of the invention may be converted to fibers or filaments by conventional melt spinning techniques. Deniers of 2 to 15 dpf are most common. The filaments may be used as-spun(undrawn) or in a stretched (drawn or oriented) condition. Drawing to reduce denier or for increasing orientation can be accomplished by the usual procedures.

The polymer compositions of the invention can be formed into nonwoven fabrics via a number of processes. These may be roughly divided into spunbonded fabrics and those fabrics using staple fibers. These are discussed in "Encyclopedia of Textiles, Fibers and nonwoven Fabrics", Ed. Martin Grayson, John Wiley and Sons, New York, 1984, pp 252-304. The compositions described herein can be used in many such products. Spunbonded nonwovens can be prepared by spinning and laying down simultaneously into webs of continuous filaments using known methods of distributing the threadline in the desired orientation in the web plane. Such webs can be thermally bonded under suitable conditions of time, temperature and pressure to strong fabrics with tensile properties which are usually superior to those obtained with staple webs. Bonding can also be carried out by using suitable adhesives and both these methods may be used to make point bonded or area bonded fabrics. Needle punching may also be used to give the webs stability and strength. Spunbonded fabrics can also be made by melt blowing wherein a stream of molten polymer is extruded into a high velocity stream of heated air and a bonded web formed directly on a screen conveyor from the resultant fibers.

Nonwoven fabrics can also be made by direct extrusion through a rotating die into a netlike product (U.S. Pat. No. 3,959,057 J. J. Smith) or by stretching and drawing embossed films of the thermoplastic polymers (British Patent Nos. 914,489 and 1,548,865 to Smith and Staple fibers can be made into nonwovens by several processes. Most of these can be classified into (1) web preparation and (2) reinforcing ("Manual of Nonwovens", Dr. Radko Krema, Textile Trade Press, Manchester, England, pp 74-76, 1971). During web preparation, bales of staple fiber are opened and formed into a web having either a random orientation (via air, water or electrostatic deposition) or parallel or crosslaid orientation (via carding and plying). Reinforcement to impart physical integrity and useful mechanical properties can be accomplished by mechanical means such as needlepunching or hydroentanglement (where water jets move fibers out of the plane of the web and entangle them) as in the spunlaced fabrics (U.S. Pat. No. 3,485,706 to Du Pont) or by stitchbonding where a reinforcing thread is sewn through the web. (See "Principles of Stitch Through Technology" Nonwovens Fabrics Forum, Clemson University, Clemson, S.C. 1978 by J. D. Singelyn). Reinforcement can also be accomplished by adhesive bonding which includes impregnation of the web by a water based resin binder solution or dispersion and subsequent evaporation of the water leaving a fabric which is composed typically of 60-70% by weight fiber and 30-40% by weight binder. Dry adhesive powders may also be applied to the staple web prior to a heating step to produce a powder-bonded nonwoven. Webs of thermoplastic staple fibers may also be reinforced by thermal bonding in which use is made of the ability of the fibers to soften and adhere to each other upon application of heat. As with the spunbonded fabrics these may be point bonded or area bonded. Heat may be applied by hot air (known as through air bonding) or by a pair of patterned and/or flat heated rollers which form a nip through which the web passes to achieve bonding. This process may be carried out with 100% thermoplastic fibers or with blends of thermoplastic fibers with fibers which do not thermally bond in the 100% form, i.e. cotton and rayon.

In addition, useful articles can also be made by laminating, extrusion melt coating or adhesively combining the above types of nonwoven fabrics with each other, with films or with staple webs in such a way as to confer desired properties on the combined fabric.

In particular, a fabric made by extrusion melt coating a thin, pinhole-free film of the compositions of this invention on a nonwoven, made by the spunbonded process or by thermally bonding staple from fibers of this invention alone or in combination with other compostable fibers such as cotton or rayon, is aesthetically pleasing and non-fluid permeable.

The compostable polyester fibers described herein may be used in all these methods of preparing nonwovens to yield fabrics which when subjected to composting conditions will be substantially degraded. Thus staple webs of the polyester fibers, as well as blends of these fibers with cotton and rayon, may be bonded by hydro-entanglement, by needle punching, by wet resin bonding and by dry adhesive bonding. (The adhesives used should be chosen to allow the desired degradation under composing conditions).

Thermally bonded staple webs of the described compostable polyester fibers can be made in the 100% form or webs containing a significant proportion of these fibers together with cotton and/or rayon may be thermally bonded to fabrics having useful mechanical properties.

Continuous or spun yarns prepared from the compositions described herein may be used to stitch bond webs of fibers such as cotton, rayon or blends of these fibers, or wood pulp, with the compostable polyester fibers of this invention resulting in fabrics which will degrade under composting conditions.

Spunbonded fabrics can be made by thermally bonding webs of continuous fibers prepared from the compostable polyester compositions described herein, and by blow spinning, direct extrusion to nets and drawing of embossed films.

The compostable compositions described herein can be melt extruded as films to coat spunlaced nonwoven fabrics which themselves may be composed of compostable fiber alone or in combination with wood pulp, rayon or cotton.

A process for preparing ultramicrocellular and plexifilamentary products is disclosed in U.S. Pat. No. 3,227,784 (Blades et al) and durable plexifilamentary and microcellular products are described in U.S. Pat. No. 3,227,664 (Blades et al) and U.S. Pat. No. 3,081,519 (Blades et al).

Extrusion of foamed plastics has also been described, for example in Modern Plastics Encyclopedia Oct. 1990 vol 67 #11 pp 291-292. In foam extrusion, molten polymer is first mixed with a relatively small amount (e.g. 1 to 15 wgt %) of a blowing agent. The blowing agent used does not have to be a true solvent for the polymer. When the mixture is extruded, the blowing agents expand due to depressurization and/or volatilization to form a microcellular structure. Unlike in flash spinning, most of the blowing agents used do not leave but stay inside the foam. Most commonlly used blowing agents are: 1). gaseous materials such as nitrogen and carbon dioxide, 2). low boiling organic solvents such as hydrofluorocarbons (e.g. HFC0134a, 152a, 125), hydrochlorofluorocarbons (e.g. HCFC-22, 123, 141b, 142b, 124), and hydrocarbons (e.g. isobutane, pentane). In addition to these types of physical blowing agents, chemical blowing agents are also used to make foams. Chemical blowing agents decompose at elevated temperatures or through chemical reaction to generate gases. Nucleating agents which are finely divided powders such as fumed silica are usually added to encourage the formation of small uniform cells.

Nonwoven webs of the compostable compositions made by the melt blowing process may also be used as an adhesive layer between other nonwoven fabrics.

It is apparent that the fiber, film, foam, and sheet products made from compositions described herein have a great number of applications in products which are disposed of or potentially may be disposed of in composting systems. In addition the compositions have utility in objects made by injection molding, injection blow molding, thermal forming of sheets, rotational molding of powder, extrusion, and pultrusion, which desirably can be disposed of and degraded in composting systems. The following is a nonexclusive list of such end uses:

Agricultural mulch
Agricultrual mats containing seeds
Nutrients
Adhesive tape substrate
Baby pants
Bags Bag closures
Bed sheets
Bottles
Cartons
Disposable diapers
Dust bags
Fabric softener sheets
Garment bags
Garbage and lawn waste bags
Industrial bags
Labels, tags
Monofilaments
Packaging materials and structures
Pillow cases
Protective clothing
Surgical drapes
Surgical gowns
Surgical sheets
Surgical sponges
Tampon applicators
Temporary enclosures
Temporary siding
Toys
Wipes.

The invention can provide fluid impermeable sheets which are compostable in typical waste disposal facilities. Preferably these sheets should not rattle or rustle objectionably and should have strength and toughness adequate for use in personal absorbent products, such as disposable diapers.

The fibers, films, foams and nonwoven fabrics prepared from the compositions of the present invention are of particular utility in disposable diapers since in that use they have an enhanced capability of being degraded in a composting operation. Typical examples of disposable diaper constructions are given in U.S. Pat. Nos. 3,860,003 (Buell) and 4,687,477 (Suzuki et al.), the disclosures of which are incorporated herein by reference. Items which can be made of the compostable compositions of this invention include:

(1) the backsheet film, i.e., the water-impermeable outside layer, which may be a film which is 100% of the compostable composition or it may be a laminated sheet with a nonwoven or web of compostable fibers including cotton or rayon adhered to the film, or it may be a film adhered to a suitable grade of paper, (2) the topsheet, i.e., the water permeable or inner layer, which is a film of a composition of the invention or a nonwoven fabric of the compostable fiber composition or a blend of the compostable fiber of this invention with cotton or rayon fiber, having a porosity suitable for passing urine quickly to the fluid absorbing pad between the topsheet and backsheet, (3) the fastening tapes which may optionally be made from films or nonwovens of the compositions of the invention; the fastening tapes are typically coated with a pressure sensitive adhesive, (4) the frontal landing strip, which may be made from films of this invention, the frontal landing strip is typically printed with a decorative design and coated with a pressure sensitive adhesive, (5) the flexible foam optionally inserted into the diaper under modest extension to gather the waist, leg openings, and/or barrier leg cuffs may be made from polymers of this invention, (6) hot melt adhesives used to bond the diaper components to one another may be formulated to incorporate polymers of this invention, (7) the leakage shield used at the diaper waist, in front and back, may be made from films of this invention, and may be glued, thermally bonded, or sonically bonded to the topsheet or the topsheet and backsheet, (8) additives to the absorbent cellulose pulp core, which may be short fibers, fibrids, synthetic pulp prepared by flash spinning, or some other mechanically dispersable and finely divided form made from polymers or fibers of this invention, and which serve to increase wet strength of the core, particularly when superabsorbent polymers have been incorporated and pulp content subsequently reduced.

(9) other minor components of the diaper which require the combination of compostability and thermoplastic fabrication and/or processing, and

(10) diaper packaging, which may comprise a bag made of film of compositions of this invention, or paper or cardboard coated with film and/or reinforced with fibers of compositions of this invention, It will be apparent that the products of the invention may contain additives such as dyes, fillers pigments, plasticizers, etc. Indeed, use of appropriate fillers or other additives may be helpful, as an acceptable way to enhance disintegratability. Use of starch is particularly helpful, as taught in application Ser. No. 834,791, and in Example 11 herein. The incorporation of finely divided particulates has likewise been found helpful, for instance incorporating similar amounts of calcium carbonate in similar compositions. As the incorporation of large amounts of such a filler may increase the tendency of articles to embrittle to an extent that could be undesirable for certain end uses, it may be desirable to take steps such as adding a plasticizer to counter such tendency. Indeed, the addition of materials such as low molecular weight polyethylene adipate (Rucoflex Mn=2000) to particulate blends has been found to provide further advantage in accelerating disintegration of related compositions under composting conditions. Also, in regard to such filled articles, microporous films are taught by Moss in U.S. Pat. No. 4,698,372, and similar techniques may be followed with products of the present invention. Advantageous results have also been obtained by using blends with tartarates and citrates, such as dibutyl tartarate and triethyl citrate. The addition of low molecular weight polyethylene adipate (Rucoflex Mn=2000) has also been shown to reduce rattle or rustle of the films of this invention. So incorporation of appropriate additives would be expected to be advantageous for the polymers of the present invention.

TEST METHODS

Polyester glass transition temperatures, Tg, are obtained by using a Du Pont model 2910 Differential Scanning Calorimeter. Samples are heated under a nitrogen atmosphere at a rate of 20 C./min. to a temperature 10-20 C. above the melting point, then the melt is cooled using the rapid air quench capability of the instrument. The Tg is determined from the second cycle scan done at 20 C./min. using the internal software to determine the inflection point of the baseline shift.

Polymer melting point, m.p., is determined on the first heating cycle as described in Tg determination.

The temperature at which the highest endothermic peak occurs is reported as the polymer melting point.

Number average molecular weight, Mn, is determined by gel permeation chromatography (gpc) versus a standard polyethylene terephthalate sample with an Mn of 22000 and a weight average molecular weight of 44000. Polymers are dissolved in and the analysis is run using HFIP (hexafluoroisopropanol) containing 0.01M sodium trifluoroacetate as the solvent. A Waters model 150C. ALC/GPC instrument, or its equivalent, is used with two Zorbax PSM-S biomodal columns (sold by E. I. Du Pont de Nemours and Company)(or equivalent) in series at 30 C. A refractive index detector was used and data collected at 100 intervals and analyzed via software provided by the instrument supplier.

Carboxyl end groups are determined by titration of an o-cresol solution of the polymer at 115 C. with KOH in benzyl alcohol to a colorimetric endpoint using bromophenol blue as the indicator. Results are reported in eq./$10^6$ grams of polymer.

Inherent viscosity is defined in "Preparative Methods of Polymer Chemistry", W. R. Sorenson and T. W. Campbell, 1961, p. 35. It is determined at a concentration of 0.5 g/100 mil of the indicated solvent at the indicated temperature, usually HFIP at 30 C.

Tensile Properties of fibers and yarns are coded as T/E/M/To for tenacity, elongation, initial modulus, and toughness and are reported in their conventional units of grams per denier, percent, grams per denier, and grams per denier. These are measured on conditioned (65% RH, 70 F) samples (3 inch gauge length) in a commercial testing machine at the rate of extension of 50% per minute (unless otherwise indicated). Toughness (To) is measured as the integrated area under the stress-strain curve. Any counterpart properties of fabrics are similarly coded as T/E/M/To and are reported in units of lb./in./oz./sq.yd., percent, lb./in./oz./sq.yd., and lb./in./oz./sq.yd., respectively. Fabric samples are 1 inch ×8 inches (with 5 inches gauge length), are conditioned prior to testing, and are extended in a commercial testing machine at a rate of 100% per minute. Paper laminates in Examples 6 and 7 are tested as 1 inch wide strips at a 5 inch gauge length at 100% E/min after conditioning at 65% RH 70 F. Results are reported as T/Emax/Eult/M/To (Tenacity at maximum load/Elongation at that load/Ultimate elongation at break/Initial Modulus/Toughness). The corresponding units are lb/in/oz/yd$^2$, percent, percent, lb/in/oz/yd$^2$ and lb/in/oz/yd$^2$, respectively.

Relative viscosity is the ratio of the viscosity of a solution of 0.8 gram of polyester dissolved in 10 ml of hexafluoroisopropanol (HFIP) containing 80 ppm $H_2SO_4$ to the viscosity of $H_2SO_4$-containing HfIP itself, both measured at 25 C. in a capillary viscometer and expressed in the same units.

Crimp index is measured by straightening a crimped tow by application of about 0.1 gpd load. Then 0.5 gm clips 66.6 cm apart are attached to the extended tow. The tow is then cut 11.2 cm beyond each clip to give a sample of 90 cm extended length. The sample is suspended vertically, hanging freely from one of the clips to allow retraction to crimped length. After about 30 secs., clip to clip distance is measured.

$$\text{Crimp Index} = \frac{(66.6 - Lc)}{66.6} \times 100$$

where Lc is the clip-to-clip distance in the free-hanging state.

Crystallinity index is measured by first obtaining a diffractogram as described by Blades (U.S. Pat. No. 3,869,429, col. 12) with some modifications. The high intensity X-ray source is a Phillips XTG-3100 with a long fine focus copper tube. Diffraction is analyzed with a Phillips single axis goniometer equipped with a thetacompensating slit and a quartz monochromator set to exclude copper $K_b$ radiation. Diffracted radiation is collected in step scanning mode in 0.025 steps with a 1.5 sec. per step count time. The digital data so collected are analyzed by a computer and smoothed by a running fit to second order polynomial. The computer is programmed to define a straight base line which joins the diffractogram tangentially at about 113 and 343. Crystallinity index is defined as $$\frac{A \times 100}{A - B}$$

where A is the intensity of the 180° 010 peak above this base line and B is the intensity of the 20° minimum above this base line. Crystallinity index has been related to percent crystallinity determined by density (see U.S. Pat. No. 4,704,329, col. 8,9). Weight percent crystallinity=0.676×Crystallinity index.

The invention will be further illustrated by the following Examples wherein, unless otherwise indicated, parts and percentages are by weight and the polymer compositions are mole %, using the same abbreviations. The "Hydrolysis" results are generally after boiling in water at 100 C. for 24 hours, except as indicated, and show reductions in molecular weight (MN), as percentages.

EXAMPLE 1

The polyester compositions [using the abbreviations herein], and the tensile properties [using the abbreviations of our copending applications] of the extrudates and hydrolysis data [given as molecular weight (Mn), initially (Init.), after 24 hours (24 Hr), and percentage loss in molecular weight after hydrolysis for that period (%)] are set out below in Tables 1A and IB. The following description of the preparation of polymer for item 11 of Table 1A of the technique used, also for items A, 3, 9, 10, 12-16, and B1-B3.

Copolyester resin ll of Table 1A was made to have the following composition:
77.8 mole % T
20.1 mole % 6 (adipic)
2,1 mole % 5SI
100 mole % 2G.

Some deviation in composition may result from generation of DEG as a byproduct during polymerization and its incorporation in the copolymer in minor amounts.

In a 35 gallon reactor containing a stirrer, a nitrogen inlet and a distillation column was placed:
44905 grams dimethyl terephthalate
36922 grams ethylene glycol
10432 grams dimethyl adipate
1859 grams 5SI dimethyl ester
29 grams $MN(OAc)_2.4H_2O$
20.4 grams $Na(OAc).3H_2O$
17 grams $Sb_2O_3$ The temperature of the reactor was slowly increased. Distillate (methanol) was collected in the amount of 17,000 ml between 160 C. and 207 C. A second distillate (ethylene glycol) in the amount of 8,300 ml was collected between 207 C. and 240 C. The resulting oligomer was transferred to a second vessel containing an agitator and vacuum capabilities. Then 17.2 grams of 85% phosphoric acid were added to the transferred material, the temperature raised to 275 C. and the maximum vacuum (0.9 mm Hg) established over 90 minutes. After 4 hours at these conditions, the contents of the reactor were discharged through a strand die into water quench and then cut into pellets.

If so desired, adipic acid may be added in the form of a low molecular weight polyethylene adipate (Rucoflex ® S-101-55, Mn=2000). Item 10 was prepared using this modification to the above procedure.

The polyester preparation of item 19 is described hereinafter in Example 5.

The technique used to prepare remaining items 1, 2, 4–8, 17 and 18 was essentially as described in Example 1 of U.S. Pat. No. 5,053,482.

TABLE 1A

| | Composition DEG/(5)/5SI | T/E/M/To gdp/%/gpd/gpd | Mn Init. | Mn 24Hr | % |
|---|---|---|---|---|---|
| 1 | 20/5/1.6 | .23/1.9/14/<.01 | 21990 | 4370 | 80 |
| A | 10/20/0 | .34/2.4/18/<.01 | 24175 | 20000 | 17 |
| 2 | 20/20/1.6 | .27/3.2/13.9/<.01 | 20295 | 11585 | 43 |
| 3 | 18.6/10(6)/2 | .61/367/19.5/1.49 | 37465 | 5760 | 85 |
| 4 | 10/10/1.6 | .18/4.1/12.4/<.01 | 36880 | 4950 | 87 |
| 5 | 0/40/1.6 | <.01/84/.07/<.01 | 37545 | 4275 | 89 |
| 6 | 10/30/1.6 | .04/745/.08/.34 | 32605 | 5040 | 85 |
| 7 | 10/40/1.6 | .02/69/.19/<.01 | 24550 | 5670 | 77 |
| 8 | 20/40/1.6 | .01/172/.12/.02 | 35065 | 3840 | 89 |
| 9 | 10/20/2 | .74/314/13./1.25 | 40490 | 3405 | 92 |
| 10 | 0/20(6)/2 | .86/604/14./2.5 | 44380 | 3270 | 93 |
| 11 | 0/20(6)/2 | .79/433/16./1.84 | 31135 | 4260* | 86* |
| 12 | 0/20(6)/2 | .71/560/15./1.95 | 43200 | 4285* | 90* |
| 13 | 10/30/2 | .70/580/.04/1.5 | 54820 | 3205 | 94 |
| 14 | 10/40/2 | .48/104/.13/.23 | 30385 | 3405 | 89 |
| 15 | 10/25/2 | .71/298/.54/1.16 | 37500 | 3400 | 91 |
| 16 | 5/25/2 | .41/690/1.2/1.16 | 39140 | 3680 | 91 |
| 17 | 0/20 + HT/2 | .06/862/.01/.18 | 27400 | 3860 | 86 |
| 18 | 0/20(6) + HT/2 | .09/983/.09/.33 | 31740 | 4500 | 86 |
| 19 | 20/21(6,5)/2 | .4/669/5.4/1.29 | 34570 | 5010** | 86** |

TABLE 1B

| | Composition DEG/PEG/(5)/5SI | T/E/M/To gpd/%/gpd/gpd | Mn Init. | Mn 24Hr | % |
|---|---|---|---|---|---|
| B1 | 7/7/17/2 | .12/331/.6/.3 | 37940 | 7110 | 81 |
| B2 | 6/6/12/2 | .41/1087/.06/1.37 | 42800 | 8310 | 81 |
| B3 | 5/5/10/2 | .54/752/1.2/1.53 | 42960 | 8110 | 81 |

As can be seen, Table 1B shows polymers that contain a proportion of PEG (the mole % has been indicated) in addition to a proportion of glutaric acid, but the procedures are otherwise essentially as in Example 5 of Application Ser. No. 07/645,849. Table 1A indicates polymers that are similar, but do not contain PEG. The aliphatic acid indicated was glutaric acid, except that the (6) indicates adipic acid, in items 3, 10–12, and 18.20 mole % of hexahydroterephthalic acid (HT) was used in addition to 20 mole % of glutaric acid or adipic acid, respectively, in items 17 and 18. Item 19 is a polymer having the composition 2G/DEG(80/20)-T/DBE-3/5SI(77/21/1), where DBE-3 is a 90/10 mixture of dimethyl adipate and dimethyl glutarate that is commercially available from Du Pont. The hydrolysis of this item and of items 11 and 12 have asterisks (*) because item 19 was hydrolysed at 60 C. for 7 days, and items 11 and 12 were hydrolysed at 100 C. for 8 hours, whereas other items in the Table were hydrolysed at 100 C. for 24 hours.

In addition, a copolymer of 4G-T/I/9/5SI (with molar proportions for the acids, respectively, 83/13/2/2) was similarly made to provide corresponding tensile properties, respectively, of 0.57/384/1.4/1.1, and Mn hydrolysis data, respectively, of 21630/3425/84%.

It will be noted that the hydrolysis was generally excellent for the polyesters of the invention, in contrast with only 17% for A, which was a comparison, containing no 5SI. The Toughness (To) of some films was excellent, whereas other items were not so tough (but generally hydrolysed quite rapidly).

2G-T compositions with 40–60 mole % of combined DEG and glutaric acid content, with at least 30 mole % glutaric acid, and 1.6 mole % 5SI, are rubbery and useful as adhesives. Using adipic acid in place of glutaric acid is expected to give similar results.

EXAMPLE 2

This Example shows the use of a low melting, water insoluble, polyester composition as a degradable compostable hot melt adhesive.

A 2G-T/5/5SI (58.4/40/1.6) polymer was prepared using the general procedure of Example 1 in U.S. Pat. No. 5,053,482.

In a 500 cc 4-necked resin kettle, fitted with a mechanical stirrer, condenser, distillation head with receiver flask, and a capillary $N_2$ inlet tube, were placed: 
93 g ethylene glycol (2G) 
0.092 g Mn(OAc)$_2$.4H$_2$O (150 ppm) 
0.099 g Sb$_2$O$_3$ (300 ppm) 
This was warmed to 160 C. to bring the contents of the flask into solution and the following were added: 
85.1 g Dimethyl terephthalate (DMT) 
48.1 g dimethyl glutarate (5 ester) 
3.56 g sodium salt of 5SI 
The temperature was gradually raised to 220 C. while methanol distillate was collected. Then 0.45 ml of a H$_3$PO$_4$ solution (4.79 g of 85% H$_3$PO$_4$ diluted to 50 ml with ethylene glycol) was added. The resultant molten monomer was poured into a polymer tube to fill it about ⅔, a capillary inlet tube drawn to a fine point was inserted to reach to the bottom of the tube, and a filter flask was attached to the sidearm of the tube to act as a receiver. Polymerization was carried out by heating the tube in a dimethyl phthalate vapor bath (284 C.), first under laboratory vacuum for about 1 hour, and then down to 0.5 mm Hg, and held for 2 hours. The capillary was removed from the molten polymer, and, after cooling, the polymer was recovered from the tube and ground into small particles in a Thomas mill using liquid nitrogen to embrittle the polymer. This flake, when dried at 100–130 C. under laboratory vacuum, coalesced to a solid block. The melting point was 114 C.

Portions of the polymer were pressed into films at 100 C. between polytetrafluoroethylene films and evaluated as a melt adhesive between strips of the degradable non woven fabric described in Example 1 of application Ser. No. 07/645,849. At 130 C., a 2 mil thick, about ¼" wide, film formed a bond so strong as to tear the fabric when pulled across the bonded area. After these bonded strips had been immersed in water for four days, the bond was still so strong that the fabric tore before the bond broke. When a film of this material was kept at 60 C. in a water bath for 1 week, the Mn was reduced from 31195 to 4805.

Similar adhesive tests were run with:
2G/DEG(90/10)-T/5/5SI(58.4/40/1.6), mp 129 C.
2G/DEG(80/20)-T/5/5/5SI(58.4/40/1.6), mp 102 C.
2G/DEG(90/10)-T/5/5SI(68.4/30/1.6) mp 138 C.

To modify the melting and adhesive properties of the polyesters, one may blend them with plasticizers and/or tackifiers.

EXAMPLE 3

This Example shows the spinning to a fiber and hydrolysis testing of the fiber from the 2G-T/6/5SI(78/20/2), polymer prepared as item 11 in Table 1A of Example 1.

Fiber Spinning

The ground polymer was dried overnight under laboratory vacuum at about 90 C., then molded into a ⅜" diameter plug, which was placed in a press spinning apparatus and spun through a 5 hole-(0.015 inch×0.045 inch) spinneret at 231 C. The filament yarn was led first around a pair of takeup rolls running at 400 m/min, then over a heated (70 C.) pin, about ¾" in diameter, to draw rolls running at 500 m/min, and then onto a bobbin. The filaments average 4.3 dpf with T/E/M-/To=1.9/67/16/0.9.

Hydrolysis of the fibers by boiling fibers deionized water and removing samples after 2, 4, 8 and 24 hrs, gave the following Mn values: initial, 46170; 2 hrs, 6940; 4 hrs, 5120; 8 hrs, 3410; 24 hrs, 3000. When hydrolysed at 60 C. in water, using a scaled flask on a thermostated shaker platform, the Mn values were: after 1.33 days, 7100; 7 days, 4520; 14 days, 4920; 25 days, 4050.

EXAMPLE 4

This Example demonstrates the preparation of foamed fibers from the same polymer as in Example 3.

The apparatus used consists of two high pressure cylindrical chambers, each equipped with a piston which is adapted to apply pressure to the contents of the vessel. The cylinders have an inside diameter of 1.0 inch (2.5 cm) and each has an internal capacity of 50 centimeters. The cylinders are connected to each other at one end through a 3/32 inch (2.3 mm) diameter channel and a mixing chamber containing a series of fine mesh screens used as a motionless mixer. Mixing is accomplished by forcing the contents of the vessel back and forth between the two cylinders through the motionless mixer. A spinneret with a quick-acting means for opening the orifice is then attached to the channel through a tee. The pistons are driven by high pressure water supplied by a hydraulic system.

In operation, the apparatus was charged with polymer pellets and solvent, then high pressure water, e.g. 1200 psi, was introduced to drive the piston to compress the charge. The contents were then heated to mixing temperature and held at that temperature for about an hour or longer, during which time an alternating differential pressure of about 100 psi or greater was established alternatively between the two cylinders to force the contents through the mixing channel back and forth, from one cylinder to the other, to provide mixing and effect formation of a solution. The solution temperature was then set to the desired spin temperature, and held there for about 15 minutes to equilibrate the temperature. Mixing was continued throughout this period. Finally, the spinneret orifice was opened, and the resultant flash-spun product collected.

| | |
|---|---|
| Polymer | 2G-T/6/5SI(78/20/2) |
| Polymer concentration: | 65% |
| Solvent | CH$_2$Cl$_2$ |
| Additives | 1% Cab-O-Sil |
| | N70TS (based on polymer wgt) |
| Mixing Temperature: | 180 C. |
| Mixing Pressure: | 1200 psig |
| Spin Temperature: | 180 C. |
| Spin Pressure: | 500 psig |

The fiber obtained was about 0.033" in diameter and about 3500 dpf., i.e., about 46% void volume.

The hydrolysis of this fiber in 60 C. water as described in Example 3 showed a decrease from an initial Mn of 29660 to 5910 in 3 days, 4700 in 7 days and 4170 in 12 days.

EXAMPLE 5

This Example demonstrates the preparation of a copolyester fiber of the invention from ingredients which include a commercially available mixture ~90/10 dimethyl adipate/dimethyl glutarate (DBE-3, referred to Example 1 above), and hydrolysis testing of the fiber.

Using a conventional four-vessel continuous polymerization system for polyester coupled to a spinning machine, polymer was prepared and melt-spun into filaments. The acid ingredients used were dimethyl terephthalate, DBE-3 and sodium dimethyl isophthalate 5-sulfonate (5SI). Diethylene glycol, (DEG) was not added as an ingredient but was generated during polymerization. Analysis showed that the polymer composition was 2G/DEG(80/20)-T/5/6/5SI (77/2/19/2). DBE-3 and 5SI were added to a mix tank containing ethylene glycol and catalysts. The catalyst was a mixture of manganese acetate, antimony trioxide, sodium acetate, and tetrapropyltitanate in a mole ratio of 4.6/4.3/1.7/1, respectively. The entire mixture was continuously fed from a mix tank to a first vessel, where ester interchange was carried out and diethylene glycol formed. The temperatures in this vessel ranged from approximately 65 C. at the top of the column to approximately 236 C. at the bottom. The vessel was operated at atmospheric pressure with a hold-up time of about 65 minutes. Dimethyl terephthalate in molten form was directly metered into the first vessel. Pure uncatalyzed glycol was metered into the vessel to adjust the catalyst level to approximately 110 ppm Mn based on the polymer to be formed. The molar proportion of ethylene glycol to the acid components was approximately 2:1.

To the liquid monomer product of the ester interchange vessel was added sufficient phosphoric acid to give approximately 120 ppm phosphorus, based upon polymer, and a sufficient amount of a slurry of 5% TiO$_2$ in ethylene glycol to give approximately 0.3% of the delusterant in the polymer. The mixture was then transferred to a second vessel, where the temperature is increased to about 243 C. and the pressure reduced to about 100 mm Hg as polymerization is initiated for about 26 minutes in the conventional manner. Excess glycol, including ethylene glycol and diethylene glycol, was removed through a vacuum system.

The low molecular weight material was then pumped to a third vessel, where the temperature was increased to about 268 C. and the pressure reduced to about 60 mm Hg. Excess glycol was again removed through a vacuum system over a period of about 12 minutes.

The low molecular weight material was then transferred to a fourth vessel, where the temperature was controlled at approximately 277 C. and the pressure reduced to 3-5 mm Hg. The pressure was automatically adjusted to maintain the polymer melt viscosity determined by an in-line viscometer. After about 200 minutes, the polymer was recovered, and found to have a relative viscosity (RV) of approximately 17.

The polymer was then spun into amorphous monocomponent filaments by extruding through orifices (of about 0.38 mm diameter) of a spinneret maintained at 260 C. As the filaments left the spinneret, they were quenched with air at 21 C., collected into a bundle, and then about 0.4% of a spin finish was applied. The filaments were wound at 1050 yards per minute to give a yarn containing 900 filaments and a total denier of 6700.

Bundles of yarn were collected to form a tow of approximately 36,000 filaments, which were drawn in a single stage at a draw ratio of about 3.3×. The fibers were crimped in a stuffer box crimper, and heat-set under essentially no restraint in an oven for 8 minutes at 72 C. The resultant filaments had a denier of 2.0, a tenacity of 2.4 grams/denier, an elongation of about 86%, a crimp level of 13-14 crimps per inch, and a crimp index of approximately 17.

The initial Mn of the fiber (average of 2 determinations) was 34220. Hydrolysis of the fiber at 60 C. in water for 1 day, reduced Mn to 9290 (avg of 2 det.), and after 2 days to 6480 and only powder remains, and after 7 days to 4960.

EXAMPLE 6

This Example shows the preparation of calendared laminates with different types and weights of paper using a degradable film of composition (2G/DEG(90/10)-T/5/5SI(73/25/2).

Details of the various papers are given in Table 6A:

TABLE 6A

| | | Paper Basis Wt/thickness oz/yd$^2$/mils |
|---|---|---|
| 1. | Towel (Scott. VIVA) | (1.2/6) |
| 2. | Towel (G.P. Sparkle) | (1.3/10) |
| 3. | Toilet Tissue (Charmin) | (0.9/6) |
| 4. | Wrapping Tissue (white) | (0.5/2) |
| 5. | Newsprint | (1.5/4) |
| 6. | Kraft (Recycled) | (2.8/6) |

The laminates were prepared by making an assembly of a film, approximately 0.5 mil thick, and coated on release paper, in contact with a similar-sized sheet of paper to be coated, and then passing this assembly through the nip between a heated polished metal top roll and an unheated resilient (silk) roll at a surface speed of 5 yd/min. at a temperature of 200 F. and under a pressure of 10 tons.

Details of the tensile properties, and of the basis weight and thickness measurements of the laminates are given in Table 6B for the same papers number 1-6, according to the invention.

Comparison samples, numbered 7 to 12 in Table 6B, corresponding to numbers 1-6, respectively, were prepared similarly, except using a coating copolyester with 2G/DEG/PEG 600(86.4/6.5/7.1)-T-5SI(98/2), i.e. not according to the present invention.

TABLE 6B

| Sample | Basis wt/Thickness (oz/yd2/mils) | | T/Emax/Eult/M/To lg/in/oz/yd2/% |
|---|---|---|---|
| 1 | 1.7/3 | MD | 2.8/22.1/50/86/.41 |
|  |  | XD | 1.6/11.5/27/90/.14 |
| 2 | /3 |  |  |
| 3 | 1.5/3 | MD | 1.4/20.4/39/62/.22 |
| 4 | 1.1/2 | MD | 5.6/2.7/19/481/.088 |
|  |  | XD | 3.8/6.9/30/221/.18 |
| 5 | 2.0/3 | MD | 8.9/1.3/1.5/844/.043 |
|  |  | XD | 3.8/3.3/3.5/282/.074 |
| 6 | 3.3/6 | MD | 10.9/2.2/2.3/871/.12 |
|  |  | XD | 13.5/4.3/4.7/300/.11 |
| 7 | 1.6/4 | MD | 2.3/18.5/48/68/.28 |
|  |  | XD | 1.4/10.4/43/82/.11 |
| 8 | /3.5 |  |  |
| 9 | 1.2/3 | MD | 1.4/3.4/24/116/.03 |
| 10 | 1.0/2 | MD | 4.0/5.7/14/279/.15 |
|  |  | XD | 4.8/3.1/16/378/.09 |
| 11 | 1.9/3 | MD | 8.0/1.2/1.6/800/.031 |
|  |  | XD | 3.7/2.7/3.1/273/.056 |
| 12 | 3.2/6 | MD | 10.6/2.2/2.2/843/.11 |
|  |  | XD | 4.6/4.2/4.6/332/.12 |

Pieces of the laminates (3-~8"×8") were placed in a rotary composter with about 0.5 cu yd$^2$ of mixed municipal solid waste (from which glass, cans and much of the light plastic and paper had been removed) and sewage sludge in the ratio of about 2/1. The composter was rotated once a week and the temperature and moisture content monitored. After 1 week temperature was 60 C., moisture 46.9%: after 2 weeks they were 48.9 C., 47.2%; after 3 weeks 32.2 C., 56.9%. After 4 weeks the compost was removed and the samples retrieved by hand sorting. Table 6C gives the results. (Notice that samples 2-6) with the coating of this invention showed the most disintegration).

TABLE 6C

| Sample | #rec | Appearance |
|---|---|---|
| 2 | 2 | Fragments of coating with traces of paper |
| 3 | 2 | Fragmented pieces of coating with traces of paper |
| 4 | 3 | Torn and perforated coating with traces of paper |
| 5 | 3 | Pieces missing from sheets, paper still adhering |
| 6 | 2 | Sheets intact except for a few holes Brittle |
| 8 | 3 | Coating intact. 10-20% degraded paper still attached. |
| 9 | 2 | Coating torn but intact. Traces of paper adhering |
| 10 | 3 | Coatings degraded on edges. Traces of paper adhering |
| 11 | 3 | Sheets intact. Edges degraded |
| 12 | 2 | Sheets intact. Paper embrittled |

EXAMPLE 7

This Example describes extrusion-coated paper laminates, using the extrusion-coating procedure and apparatus described in Example 1 of application Ser. No. 07/645,849, with temperatures in degrees F. The polymer compositions are given in the Table 7A for the components other than 2G-T. The polymer of item 3 was prepared by a method similar to that of Example 5 herein, while the others were prepared by methods similar to that of Example 1 of application Ser. No. 07/645,849.

The resin was placed in a hopper above the inlet of a 1 inch (2.5 cm) extruder (Echlin Mfg. Company Serial #0717) with an 18 inch wide film die with a 0.007 inch gap. An 18 inch wide non woven fabric was led continuously at a speed of 47–106 ft/min through an extrusion coating machine made by Bertek Inc. of St. Albans, Vt. The paper to be coated (2 ply, 11 inch wide roll of household paper towel-Bounty brand made by Procter & Gamble Cincinnati, Ohio 45202) was fed over this support fabric, and the assembly was led through a corona treatment (made by Intercon), through an S-warp between two 4 inch diameter rolls, heated to 150–260 F., onto a polytetrafluoroethylene-coated, matte-finished chill roll of diameter 12 inches (30 cm), at 100–200 F., around 300 degrees of the circumference of this 12 inch diameter roll, while the resin was extruded through the die at a delivery rate found appropriate to yield a coating of the desired thickness, at a position between the chill and nip rolls as close as possible to the chill roll (about 0.25–0.5"). The polymer temperatures in the extruder (Ext) and in the die are given in Table 7A, and were adjusted to minimize flow irregularity. A film with 0.5 mil thickness was applied to the paper. When the barrier (film-coated) side of these laminates were coated with a water or iso propyl alcohol solution of red dye, no penetration was noted.

TABLE 7A

| | Composition DEG/PEG/(5)/5SI | Temp (F.) Ext/Die |
|---|---|---|
| 1 | 6/6/12/2 | 411/408 |
| 2 | 5/5/10/2 | 379/428 |
| 3 | 6/6/10/2 | 369/375 |
| 4 | 0/0/20(6)/2 | 424/422 |

Item 4 contains adipic (6) residues, whereas the others contain glutaric (5) residues. The tensile properties were measured for item 4 (basis weight 1.7 oz/yd$^2$) as follows:
T/Emax/Eult/M/To:
MD-2.0/14/24.8/75/0.34;
XD-1.6/8/29/73/0.31

Six strips (1 inch×8 inches) of Items 3 and 4 were placed in the composter described in Example 6. After 28 days the samples were retrieved to show the following results:

TABLE 7B

| Sample | # rec | Condition | Zero Gage B.S. (lbs) | (% lost) |
|---|---|---|---|---|
| 3 | 5½ | Darkened | 1.06 | 66 |
| 4 | 5 | Edges eroded | 1.86 | 51 |

Thus significant loss in strength of these extrusion coated laminates was observed after composting.

EXAMPLE 8

This Example describes preparation of extrusion-coated nonwoven fabrics, essentially as described in Example 7, except that the coating was extruded directly onto non-woven fabrics instead of onto paper.

The resin had been previously crystallized and then dried as described hereinbefore, and sealed in airtight bags, and was poured from such bags directly into the hopper to minimize contact with air. The hopper was sealed, and the resin was preheated by recirculating dry, hot air (air temperature 100–150 deg F., <−20 deg F. dew point) for 1 hour prior to extrusion.

Various 18 inch wide nonwoven fabrics, prepared by thermally bonding carded webs of the following fibers and fiber blends, were led continuously through an extrusion coating apparatus made by Bertek, Inc. of St. Albans, Vt. at speeds of 47–107 ft/minute, depending on coating thickness. The fabrics were:
  A. 100% polyester of the composition disclosed in Example 2 of U.S. Pat. No. 5,053,482
  B. 100% polyester of the composition disclosed in Example 1 of co-pending application Ser. No. 834,792
  C. 75%/25% by weight polyester as in B above/'East Street" cotton sold by Veratec Films of 0.5 and 0.75 mil thicknesses were applied to the nonwoven fabrics. When the barrier (film coated) side of this fabric was wet with a water or isopropyl alcohol solution of red dye, no penetration was noted.

Nonwoven fabric B coated with 0.5 mil of composition DEG/(5)/5SI 10/25/2 ((Item 15, Table 1A)) was composted in a municipal co-composting IPS facility in Fairfield, Conn., in a mixture of shredded yard waste and sewage sludge (1:1 sludge:yard waste). The compost was turned once every working day, had an initial moisture content of 60% and a neutral pH. Forced aeration was used to control the temperature, with actual temperature of the compost running from 43–65 deg C. for the 21–24 day composting cycle. At the end of the composting cycle, the residual fragments of coated nonwoven fabrics were recovered. Upon examination, virtually all of the film coating of Item 15, Table A had physically disintegrated and disappeared from the nonwoven fabric. It was impossible to measure physical properties of the residual film fragments.

In contrast, when sheets of 1.2 mil polyethylene film were subjected to the same composting operation (for comparison), the polyethylene films remained intact, with minimal visual evidence of degradation or disintegration. Mechanical action reduced the average size of such composted polyethylene films 48%, and reduced MD strength 21% and CD strength 60%.

EXAMPLE 9

Films of polymer of composition 2G/DEG(90/10)-T/5/5SI(58/40/2) (14 of Table 1A) were tested, using 100% of such polymer and blends with corn starch using a Brabender as described in Example 1 (of co-pending Application QP-4850). The films were pressed as described in Example 1 Ser. No. 834,791. Samples of film about 3–4" in diameter were tagged by bolting between two marked 1"×1"×1/16" polytetrafluoroethylene sheets and placed in a rotary composter with 2/1 municipal solid waste and sewage sludge for 28 days, as described in Example 6.

The condition of the recovered samples is described in the Table below:

| Sample | Condition | Mn (Initial) | Mn (28 Days) |
|---|---|---|---|
| 100% Polymer | mostly eroded | 40920* | 18980* |
| 25% Starch | 100% eroded | | |
| 50% Starch | 100% eroded | | |

*(average of 2 determinations)

EXAMPLE 10

This Example describes the preparation of paper laminates with polyesters containing cornstarch filler and their degradation by composting.

Commercial cornstarch was dried at 70 C. in a vacuum oven and a copolymer 2G/DEG(90/10)-T/5/5SI(58/40/2), prepared by a procedure similar to that described in Example 1 herein, was dried separately under the same conditions. They were mixed in the proportions shown in the Table below and blended in a Brabender Plasticorder with the starting temperatures and for the times indicated. These blends were then pressed to films between polytetrafluoroethylene sheets, using a press with heated platens (model SPWR228C-X1-3-5-3-16-20 made by Pasadena Hydraulics Inc. City of Industry, Calif.) These films were laminated onto commercially available paper towels (Viva brand with 1.2 oz/yd² basis weight, 0.006" thick) by pressing the two together with a polytetrafluoroethylene cover sheet to prevent sticking, at 100 C. for 10–20 sec at a load of 1000 lbs.

| Polymer/Starch | Temp C. | Time | Thick | Laminate | |
|---|---|---|---|---|---|
| wt % | Init End | min. | mil | thick | B.W. oz/yd² |
| 75/25 | 147 153 | 6 | 5 | 8 | 6 |
| 50/50 | 147 155 | 6 | 4 | 9 | 4.1 |
| 25/75 | 134 160 | 9 | 10 | did not adhere well | |

The 75% starch blend was too stiff to flow readily enough (under these conditions) to form a good laminate.

Compostability of the 75/25 copolyester/starch paper laminate was evaluated by placing it in a rotary composter with mixed municipal/sewage sludge (as described in Example 6) for 4 weeks. The sample was tagged by bolting 1/16" thick × 1" square polytetrafluoroethylene washers on the laminate. At the end of the test period, all of the laminate which had been exposed had disintegrated.

EXAMPLE 11

This Example shows the preparation of starch/copolyester and starch/copolyester/biodegradable additive compositions continuously in a twin screw extruder, injection molding of some of the compositions and their evaluation in composting.

Copolyester Resin Preparation

Polymers having the following compositions were prepared in the same reactor and by procedures similar to those in Example 1 (item 11 in Table 1A) herein (some deviation in composition may result from generation of DEG as a by-product during polymerization and its incorporation in the copolymer.)

| Polymer 1 (mp 176 C.) | Polymer 2 (mp 175 C.) |
|---|---|
| 73% T | 68% T |
| 25% S | 30% S |
| 2% 5SI | 2% 5SI |
| 90% 2G | 100% 2G |
| 10% DEG | |

The polymer pellets were dried overnight in a large tray dryer at 80 C. with hot dry air recalculation to a moisture content of less than 0.04%.

Corn starch (Corn Products 3005 from CPC International, Inc.), and rice starch (Sigma Chemicals catalogue #S7260) were dried overnight in a large tray vacuum oven at 90 C. and less than 1 mm Hg vacuum to a moisture content of less than 1%, and stored in sealed containers until used.

Polyethylene adipate (RUCOFLEX® S-101-55, nominal molecular weight × 2000, from Ruco Polymer Corporation) was used directly without pretreatment.

Blends of polymer pellets and starch were made by manually tumbling the materials in plastic bags. The dry (room temperature) starch was added to warm polymer pellets from the dryer, and the (still warm) mixture fed to the extruder. When polyethelene adipate (RUCOFLEX) was used, the polymer and RUCOFLEX were blended first to assure uniform distribution of RUCOFLEX in the warm polymer prior to addition of the starch.

The following compositions were made:
A 60% polymer 1, 40% cornstarch
B 60% polymer 1, 40% rice starch
C 55% polymer 1, 40% cornstarch, 5% RUCOFLEX
D 60% polymer 2, 40% cornstarch
E 60% polymer 2, 40% rice starch
F 55% polymer 2, 40% rice starch, 5% RUCOFLEX The blends were placed in the feed hopper (with nitrogen purge) of a Ktron twin screw feeder (Model #T-35 with 190 6300 controller) and metered to a Werner and Pfleiderer ZSK 30 mm twin screw extruder. This extruder had an L/D of 30/1 with a vacuum port and a mild mixing screw. The temperature of the extruder barrel was electrically heated from 165 C. at the feed end of the extruder to 190 C. at the discharge. The extruder was operated at 150 RPM, and the vacuum port was connected to house vacuum and permitted to fluctuate with process conditions. A single hole die (⅛" dia.) is used for discharge. The resulting strand was quenched in a 6 ft long water trough, dewatered with an air knife and cut into pellets with a Conair cutter (Model #304). Specific operating conditions for the individual compositions are listed below.

| Comp. | Feed Rate PPH | Screw Torque % max | Die Pressure PSIG | Melt Temp C. | Vacuum In Hg | COMMENTS |
|---|---|---|---|---|---|---|
| A | 34 | 58 | 800 | 251 | 13 | ROUGH STRAND BUT FEW BREAKS |
| B | 32 | 60 | 800 | 248 | 13 | ROUGH STRANDS WITH MANY BREAKS |
| C | 31 | 52 | 750 | 241 | 12 | SMOOTH STRAND NO BREAKS |
| D | 33 | 56 | 750 | 253 | 13.5 | ROUGH STRANDS BUT FEW BREAKS |
| E | 33 | 53 | 760 | 250 | 13.5 | ROUGH STRANDS WITH MANY BREAKS |
| F | 29 | 53 | 560 | 240 | 13.0 | SMOOTH STRANDS NO BREAKS |

The RUCOFLEX® lowers die pressure and melt temperature, while improving strand surface smoothness. Samples A, B, D, and E were stiff and brittle while samples C and F were flexible and tough, showing the advantage of using the RUCOFLEX ®.

To show the utility of these compositions in aqueous environments, a piece of the extrudate from composition D was immersed in room temperature water for 91 hrs. It showed a 1.2% gain in weight, a 4.7% increase in diameter and a 1% loss in length.

Composition C and F pellets were dried overnight in a large tray drier at 80 C. with hot dry air recirculation. Each composition was injection molded, using a 6 oz Van Dorn injection molding machine with the following characteristics;
Model 125-RS-6
125 ton clamping pressure
General purpose 1.575 inch screw
Hydraulic gauge factor 10.7/1

A mold designed to produce two 5"×½"×½" standard Izod bars and one 3"×5"×1/16" plaque was attached.

The extruder heater temperature was set at 200 C. and the mold was cooled to 20 to 25 C. The injection cycle used was—1 second boost (1200 psig), 30 seconds inject (600 psig), 15 second hold (0 psig). Ram speed was operated at maximum, screw speed was 60 RPM, and screw back pressure was 50 psig.

Properties of the bars and plaques with compositions C and F, conditioned and measured at 23 C. and 50% RH, are in the following Table:

| Sample | Yield Stress (KPSI) | Maximum Stress (KPSI) | Break Stress (KPSI) | Yield Elongation (%) | Ultimate Elongation (%) |
|---|---|---|---|---|---|
| C - MD | 1.74 | 1.8 | 1.03 | 16 | 77 |
| C - XD | 2.0 | 2.0 | 1.4 | 8.9 | 96 |
| F - MD | 1.74 | 1.83 | 1.5 | 10 | 35 |
| F - XD | 1.94 | 1.98 | 1.79 | 8.9 | 37 |

| Sample | Izod Impact (FTLB/IN) |
|---|---|
| C - at gate | 0.44 |
| C - far edge | 0.46 |
| F - at gate | 0.35 |
| F - far edge | 0.33 |

One plaque and one tensile bar of compositions C and F were placed in a rotary composter (Kemp Compostumbler) with a mixture of 50% municipal solid waste and 50% municipal waste water treatment sludge and allowed to compost for 28 days, turning every week and adding water after two weeks to maintain greater than 40% moisture. The composition C plaque and bar broke into fragments during this treatment. The composition F plaque and bar were substantially intact but all the samples could easily be broken by bending. Gpc analysis of the polyester showed a 31% reduction in Mn for the Composition C bar and a 10% Mn reduction for the composition F bar. Samples recovered from a 28 day compost test were subjected to a second 28 day test, from which no samples remained in condition to be recovered.

EXAMPLE 12

It is generally desired that the cost of the degradable materials be as low as possible. For this reason, the main components of the polyesters may generally be such as are available at low cost in large volumes, such as ethylene glycol, 1,4 butylene glycol and terephthalic acid. Inclusion of a small fraction of groups such as carbonate esters generally provides enough fast degrading links so hydrolysis will result in reduction of the molecular weight of the polyester below that at which physical properties are appreciable and/or to the point that microorganisms can digest the residue.

It is known that aliphatic glycol carbonates in particular tend to decompose at temperatures which are relatively low compared to the melting points of low cost 2GT and 4GT polyesters. To avoid excessive degradation during transesterification and polymerization, copolymers of 2GT or 4GT may be chosen such as have melting points below the decomposition temperatures of the aliphatic polycarbonates used.

The poly(diethylene glycol carbonate) polyol used in some of the polymer syntheses described herein may be prepared by the reaction of ethylene carbonate with ethylene glycol or diethylene glycol as an initiator in the presence of a catalyst such as sodium stannate and purified as described in J. Poly Sci Vol 38, 463–476 (1989). Other methods of producing suitable polycarbonates include; the reaction of carbon dioxide with an epoxide (S. Inoue, H. Koinuma, and T. Tsuruta, Poly. Lett., Vol 7, 287, (1969) and Makromol. Chem. Vol 155, p 61 (1972); the reaction of phosgene with glycols; and the reaction of dialkyl or diphenyl carbonate with glycols.

So Example 12 desribes the preparation of a copolymer having the composition 2G/DEG(90/10)-T/1/5/5SI(63/10/25/2), where the "1" represents a carbonate radical, as well as a comparison of a similar composition without 5SI. An oligomer of diethylene glycol carbonate was prepared using a procedure from J. Appl Poly. Sci. Vol. 38, pp 463–476 (1989), combined with an oligomer 2G-T/5/5SI, and polymerised. Also described is the spinning of fibers from the compositions and evaluation of molecular weight reduction during exposure to water.

In a 500 ml flask, fitted with a stirrer, a thermometer, and a drying tube filled with Drierite, were placed:
200 g ethylene carbonate
4 g ethylene glycol
1 g sodium stannate trihydrate This was heated and stirred at an internal temperature of 135 C. for 114 hours. The cooled mixture was dissolved in 500 ml of acetone. 5 g of talcum powder was added and the dispersion was stirred, then filtered. The acetone was distilled off at atmospheric pressure, then the residual material was heated at 210 C. for 2 hours under 1.3 mm Hg vacuum. 62 g of viscous, brown liquid oligomer were obtained.

In a three-necked flask fitted with a stirrer, $N_2$ inlet and a distillation head were placed:
70.7 g ethylene glycol
0.079 g Mn(OAc).4H$_2$O
0.084 g Sb$_2$O$_3$ This was heated to 160 C., and stirred to dissolve the catalysts and the following were added:
73.4 g dimethyl terephthalate
24.0 g dimethyl glutarate
3.55 g sodium dimethyl 5-sulfoisophthalate The flask was heated slowly to an internal temperature of 220 C., as methanol was distilled off. The temperature was then decreased to 200 C. and 7.9 g of the above oligomer were added, and the mixture stirred for 30 min. The melt was transferred to a polymer tube which has a side arm and a finely drawn N$_2$-inlet capillary tube was inserted to the bottom of the tube. The polymer tube was heated in a glycol vapor bath (198

C.), and polymerization carried out for about 1 hr, at house vacuum, and 20 hours at 0.3 mm Hg pressure.

The polymer was spun through a 0.009" diameter hole at a delivery rate of 0.07 cc/min and wound up at 12.5 to 37.5 m/min. The 37.5 m/min sample had T/E/Mi/To=0.3/700/2/0.74 (13 dpf). The Mn by gpc is 28680. After 14 days in water at 60 C. the Mn was 8670.

A comparison fiber made similarly, but without 5SI in the copolymer, in contrast had an initial Mn of 27880 which changed only to 25560 after 14 days in 60 C. water.

EXAMPLE 13

This shows the preparation of a copolymer 2G-T/6/4SP(78.4/20/1.6), preparation of fibers, and hydrolysis of the fibers.

The copolymer was made by the following procedure:

In a 500 ml reaction kettle fitted with a distillation head, a N$_2$ inlet and a stirrer were placed:
93.0 g ethylene glycol
1.0 ml 10% tetrabutyl titanate in glycol solution
This was heated to 160 C. with stirring and the following added:
114.2 g of dimethyl terephthalate
26.1 g dimethyl adipate
3.6 g sodium dimethyl 4-sulfophthalate (4SP)

This mixture was heated slowly to 220 C. (bath temperature) and methanol distillate is collected. The molten prepolymer was then transferred to a polymer tube with a side arm and a finely drawn capillary N$_2$ inlet tube was inserted with its tip near the bottom of the tube. The polymer tube was immersed in a diphenyl ether vapor bath and polymerization was carried out by removing glycol vapor, first at laboratory vacuum for 1.5 hours, then at 0.3 mm Hg pressure for 4 hours. The polymer had a reddish color.

Fiber spinning was carried out as described in Example 3 herein through a 5 hole spinneret with 0.015" dia×0.045" long holes, at a spinneret temperature of 204-220 C. at a delivery of about 0.7 cc/min, taken up on a roll running at 40 m/min. and drawn 2× over a hot pin at 80 C. Fiber properties were T/E/M/To=0.5/317/11/0.92. Hydrolysis was carried out at 60 C. in water in a capped Erlenmeyer flask shaken in an air thermostat. The Mn was initially 20650. After 3 days it was 5480, i.e., a 73% reduction.

In comparison, a film with the composition 2G-T/6(75/25)(no 4SP) having an initial Mn of 38600 was hydrolyzed in boiling water (100 C.). The Mn after 8 hours was 38000 (2% reduction). After 24 hours it was 34200 (11% reduction).

EXAMPLE 14

This Example shows the preparation of a 2G-T/6(80/20) copolyester endcapped with 0.8 mole % sodium m-carboxy benzene sulfonate groups and its evaluation in hydrolysis vs. a copolyester of the same composition without endcapping with the sulfonate.

The polymer was made by the procedure in Example 13 with the following ingredients:
124.0 g ethylene glycol
0.3 ml 10% tetrabutyl titanate in glycol solution
26.1 g dimethyl adipate
116.5 g dimethyl terephthalate
1.5 g sodium m-carbomethoxy benzene sulfonate The polymerization was carried out in a dimethyl phthalate vapor bath for 1 hour at laboratory vacuum and 4 hrs at 0.5 mm Hg pressure. The polymer obtained had a reddish color.

A film about 4-5 mils thick was made by hot pressing some of the polymer between polytetrafluoroethylene films at 225 C. Four 1"×4" strips of film were placed in 250 ml of deionized water and refluxed for 24 hrs. One sample strip was removed after 2, 4, 8 and 24 hrs. Mn was determined on the samples by gpc with the following results:
2 hr—18060, 4 hr—16200, 8 hr—11970, 24 hr—4860.

A similar polymer made without the addition of the sodium m-carbomethoxy benzene sulfonate gave the following results on hydrolysis:
2 hr—19900, 4 hr—20180, 8 hr—18710, 24 hr—14620.

A similar, but less favorable effect was obtained was 2G-T/6(80/20) endcapped with 2 sulfo benzoate groups.

EXAMPLE 15

This shows the preparation of extruded films improved by containing a modifier to reduce "rustle".

Polymers of the compositions 2G/DEG(90/10)-T/5/5SI(73/25/2) (Polymer 8A) and 2G/DEG/PEG(Mw=600)(85/8/7)-T/5/5SI(86.2/12/1.8) (Polymer 8B) were blended with 5% polyethylene adipate (RucoFlex® S-101-55, nominal molecular weight=2000 from Ruco Polymer Corporation) by tumbling the dried polymer pellets and liquified RucoFlex® in sealed jars.

The mixture was placed in the hopper of a single screw volumetric feeder (K-tron, Model No 7) from which it free falls to the inlet of a 28 mm Werner and Pfleiderer twin screw extruder with a vacuum port (maintained at house vacuum) attached to a 10 inch wide film die with about a 0.010 inch gap. A dry nitrogen purge was maintained in the feed hopper and the feed throat of the extruder. The extruder was operated at 150 RPM screw speed with a heater temperature (C) profile of

|  | Zone 1 | Zone 2 | Zone 3 | Zone 4 | Zone 5 | Die | Melt |
|---|---|---|---|---|---|---|---|
| Comp. A | 130 | 140 | 150 | 170 | 170 | 160 | 197 |
| Comp. B | 180 | 190 | 200 | 220 | 220 | 200 | 228 |

The extruded polymer films were electrostatically pinned on an 8 inch diameter smooth quench drum maintained at 26 C. with cold water and collected on release paper using a standard tension roll. The quench drum speed was adjusted from 5 to 15 ft per minute to obtain film samples from about 8 mils to 1.5 mils thick.

In comparison to films extruded similarly from unmodified polymers these films generated much less noise when handled or shaken.

What is claimed is:

1. A fiber and film forming biodegradable polyester which undergoes hydrolytic degradation when subjected to the conditions of moisture and temperature that typically characterize composting operations to form products readily digested to innocuous materials by organisms typically found in solid waste and compost, said polyester consisting essentially of recurring structural units of the formula:

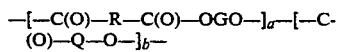

wherein about 5 to 40 mole % of R is selected from the group consisting of a chemical bond and one or more divalent, non-aromatic, $C_1$-$C_{10}$ hydrocarbylene radicals, and at least about 85 mole % of the remainder of R is p-phenylene radical, wherein G is about 1 to 30 mole % of a polyethylene ether radical selected from the group consisting of —$(CH_2)_2$—O—$(CH_2)_2$— and
—$(CH_2)_2$—O—$(CH_2)_2$—O—$(CH_2)_2$— and the remainder of G is a hydrocarbylene radical selected from the group consisting of —$(CH_2)_2$—, —$(CH_2)_3$—, and —$(CH_2)_4$-radicals, wherein Q is derived from an hydroxy acid of formula HO[—CO(O)—Q—O—]$_x$H, where x is an integer, such hydroxy acid having a melting point at least 5 degrees C. below its decomposition temperature, and Q is selected from the group consisting of a chemical bond and hydrocarbylene radicals —$(CH_2)_n$—, where n is an integer from 1 to 5, —C(R')H—, and —C(R')HCH$_2$—, wherein R' is selected from the group of —CH$_3$ and —CH$_2$CH$_3$, and wherein "a" and "b" are mole fractions of the polyester, and the mole fraction "a" may be 0.6 to 1 and, correspondingly, mole fraction "b" may be 0 to 0.4, and wherein about 0.1 to about 2.5 mole % of the polyester is composed of moieties comprising alkali metal or alkaline earth metal sulfo groups.

2. A polyester according to claim 1, wherein G is about 1 to 30 mole % of a polyethylene ether radical selected from the group consisting of —$(CH_2)_2$—O—$(CH_2)_2$— and —$(CH_2)_2$—O—$(CH_2)_2$—O—$(CH_2)_2$—, and the remainder is selected from the group consisting of polyalkylene ether radicals of molecular weight at least about 250, and —$(CH_2)_2$—, —$(CH_2)_3$—, and —$(CH_2)_4$— radicals.

3. A fiber of the polyester of claim 1 or 2.

4. A non-woven sheet of the polyester of claim 1 or 2.

5. A film of the polyester of claim 1 or 2.

6. A foam of the polyester of claim 1 or 2.

7. A composite of the film of claim 5 and of a layer of nonwoven sheet or of paper.

8. A disposable diaper which includes an absorbent body portion having on one surface thereof a water permeable sheet of the polyester of claim 1 or 2.

9. A disposable diaper which includes an absorbent body portion having on one surface thereof a water impermeable sheet of the polyester of claim 1 or 2.

* * * * *